United States Patent [19]
Youssefyeh et al.

[11] Patent Number: 4,857,517
[45] Date of Patent: Aug. 15, 1989

[54] QUINUCLIDYL BENZOXEPINS AS 5-HT₃ ANTAGONISTS

[75] Inventors: Raymond Youssefyeh, Princeton Junction, N.J.; Scott I. Klein, Audubon, Pa.; Henry F. Campbell, North Wales, Pa.; Donald E. Kuhla, Doylestown, Pa.

[73] Assignee: Rorer Pharmaceutical Corporation, Fort Washington, Pa.

[21] Appl. No.: 152,112

[22] Filed: Feb. 4, 1988

[51] Int. Cl.⁴ .................. A61K 31/625; C07D 453/02
[52] U.S. Cl. ..................................... 514/161; 514/305; 546/133
[58] Field of Search ................. 546/133; 514/161, 305

[56] References Cited

U.S. PATENT DOCUMENTS 3,103,515  9/1963  Zaugg et al. .................. 544/376 X

FOREIGN PATENT DOCUMENTS 0234872  9/1987  European Pat. Off. .

Primary Examiner—Richard A. Schwartz

[57] ABSTRACT

Certain specific substituted 9-N-(1-azabicyclo-[2.2.2.]octan-3-yl)carboxamido-2,3,4,5-tetrahydro-1-benzoxepins and their valuable use as 5-HT₃ antagonists having CNS and gastric prokinetic acticity and void of any significant D₂ receptor binding properties are disclosed. Methods for their preparation also are described.

14 Claims, No Drawings

QUINUCLIDYL BENZOXEPINS AS 5-HT₃ ANTAGONISTS

FIELD OF THE INVENTION

This invention is directed to certain specific novel chemical compounds and their valuable use as pharmaceutical agents as 5-HT$_3$ antagonists having unique CNS, anti-emetic and gastric prokinetic activity void of any significant D$_2$ receptor binding properties. This invention also describes novel processes necessary for their preparation.

SUMMARY OF THE INVENTION

This invention relates to the compounds described by general Formula I and to therapeutic compositions comprising as active ingredient a compound of Formula I:

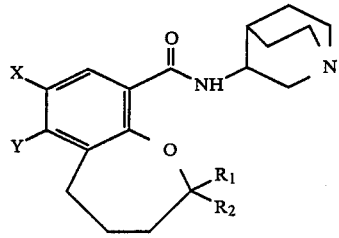

Formula I where:
X is hydrogen or halo;
Y is hydrogen, amino or loweralkylamino;
R$_1$ and R$_2$ are independently hydrogen or loweralkyl;
and pharmaceutically acceptable salts thereof.

Preferred compounds of this invention include those where:
X is halo and Y, R$_1$ and R$_2$ are hydrogen;
Y is amino or loweralkylamino and X, R$_1$ and R$_2$ are hydrogen; and
X is halo, Y is amino and R$_1$ and R$_2$ are hydrogen.

More preferred compounds include those where halo is chloro or bromo and loweralkyl is methyl.

The present compounds may be prepared by the following general procedure:

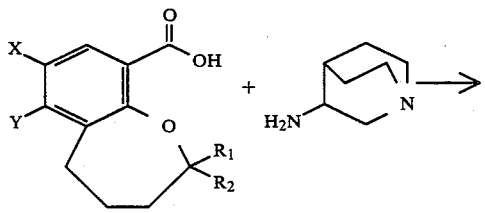

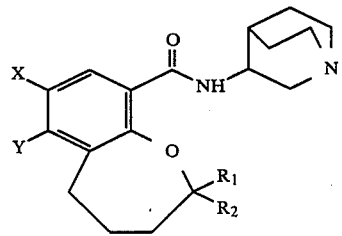

Condensation of a substituted 2,3,4,5-tetrahydro-1-benzoxepin-9-carboxylic acid, acid halide or ester with 3-amino-1-azabicyclo[2.2.2]octane results in the corresponding substituted benzoxepin-9-carboxamide. In general this reaction may be carried out at 0° C. by adding ethyl chloroformate to a reaction mixture of the acid in chloroform in the presence of triethylamine. This is then reacted with 3-amino-1-azabicyclo[2.2.2-.]octane to obtain the desired product. Condensation may also be carried out in the presence of a dehydrating catalyst such as a carbodiimide in a solvent at normal temperatures.

The starting materials, that is the substituted 2,3,4,5-tetrahydro-1-benzoxepin-9-carboxylic acids are also novel. They may be prepared by the following reaction schemes.

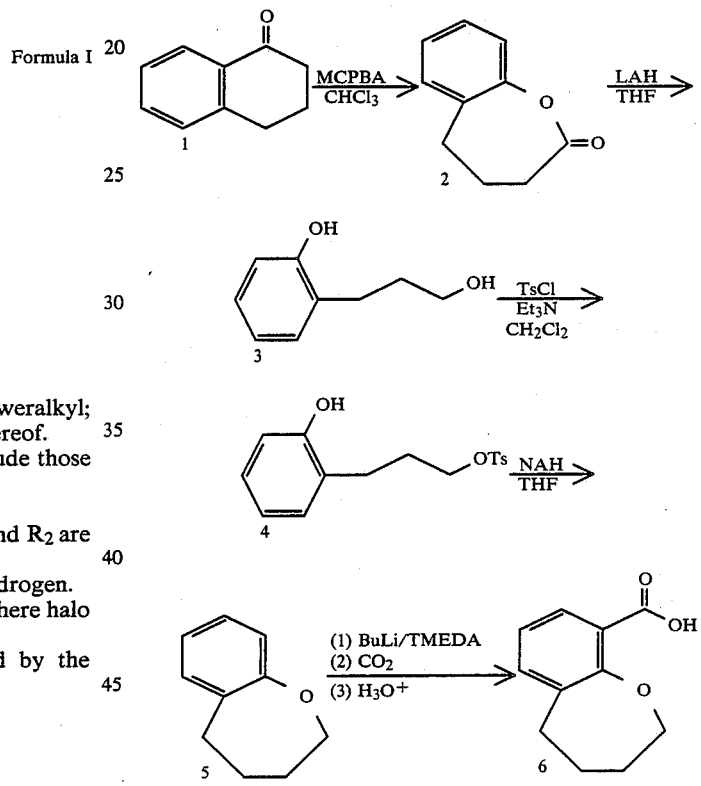

When α-tetralone(1) is treated with m-chloroperbenzoic acid the seven membered 1-benzoxepin-2-one(2) is formed. Treatment with lithium aluminum hydride in a THF solution at 0° C. opens the ring to form o-hydroxypropylphenol(3). This in turn when treated with one equivalent of tosylchloride in the presence of triethylamine forms the primary tosylate which when treated with sodium hydride in THF ring closes to form 2,3,4,5-tetrahydro-1-benzoxepin(5). Treatment of the latter with a mixture of n-butyl lithium and tetramethylethylenediamine results in the 9-lithio compound which is then carboxylated with dry ice to form the 2,3,4,5-tetrahydro-1-benzoxepin-9-carboxylic acid(6), upon acidic workup.

When R$_1$ and R$_2$ substitution is desired, the following reactions may be carried out.

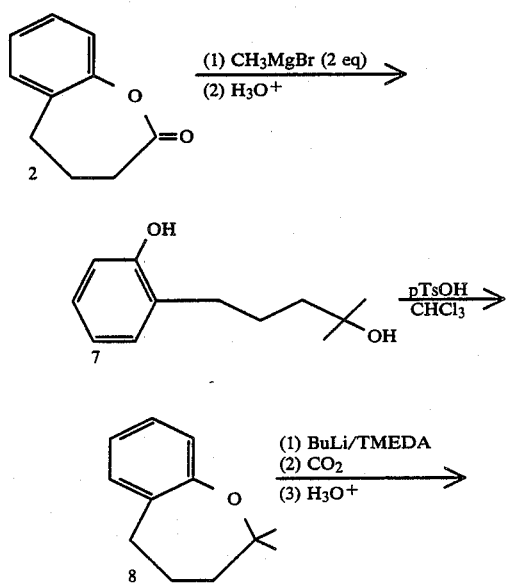

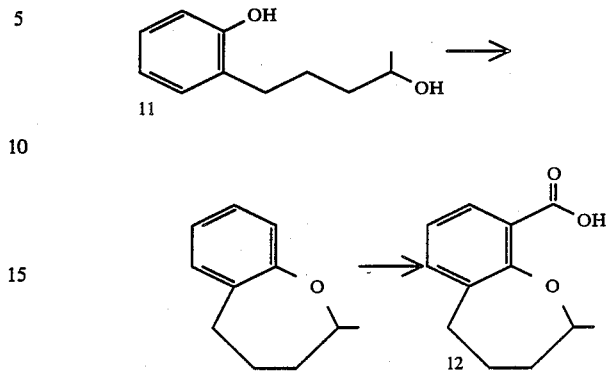

When the 9-carboxylic acids 6, 9 and 12 are treated with N-chlorosuccinimide or N-bromosuccinimide in a polar medium (DMF) at room temperature, the resulting halogenated products 13, 14 and 15 are formed.

When 1-benzoxepin-2-one(2) is treated with an excess of Grignard reagent and acidified, the ring opened diol results. Treatment with tosic acid at raised temperatures gives the 2,2-disubstituted-1-benzoxepin(8) which again upon treatment with n-butyl lithium and tetramethylethylenediamine and carbon dioxide as above gives the 2,3,4,5-tetrahydro-2,2-disubstituted-1-benzoxepin-9-carboxylic acid (9). When a controlled amount of Grignard reagent is used the resultant ring opened product is the 2-pentanone compound(10). Reduction with lithium aluminum hydride results in the diol(11). This is then treated as above to obtain 2,3,4,5-tetrahydro-2-substituted-1-benzoxepin-9-carboxylic acid(12).

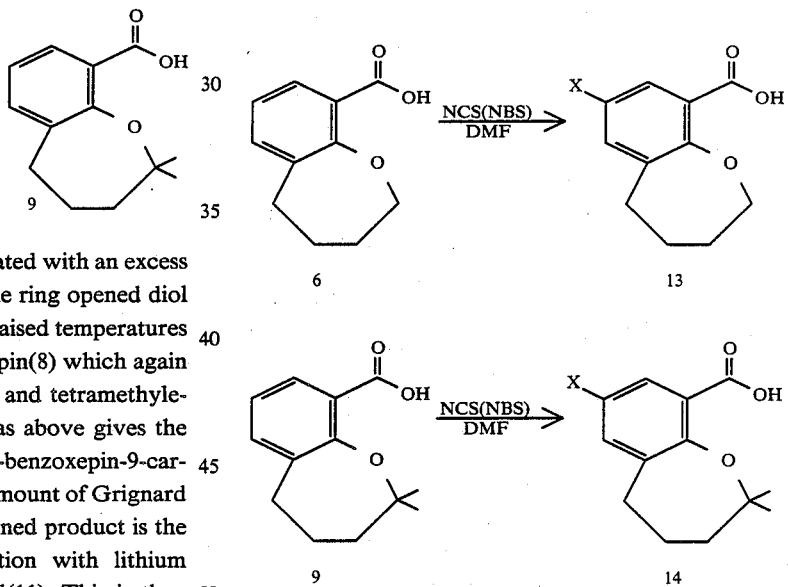

where X is chloro or bromo.

When it is desirable to have an amine or alkylamine function in the 6-position of the 1-benzoxepin ring, then the following reaction synthesis may be followed.

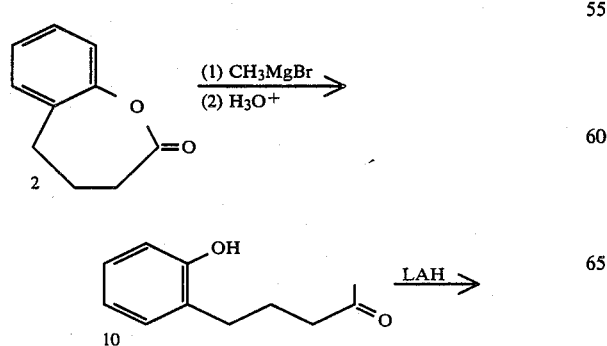

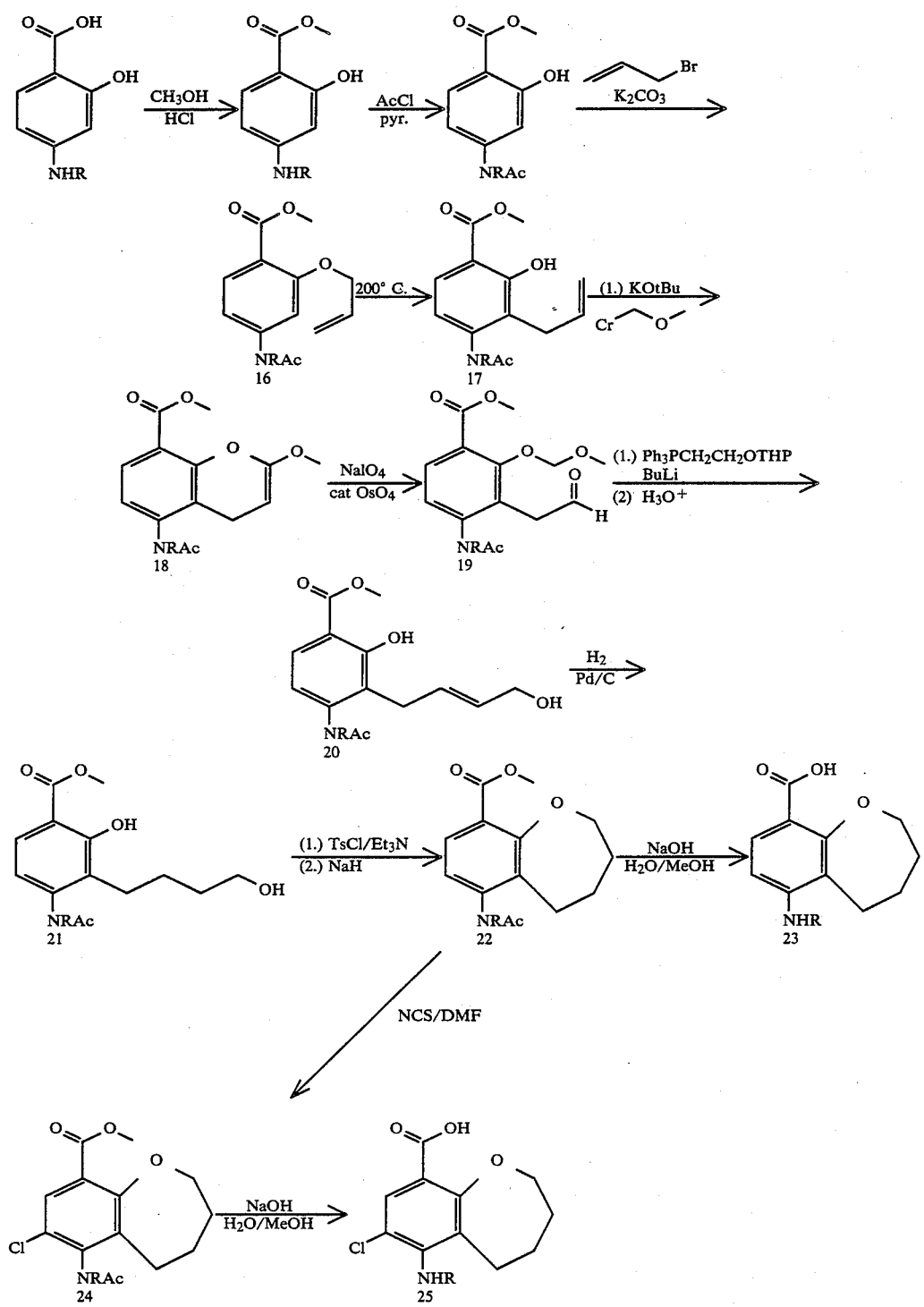

where R is hydrogen or loweralkyl.

4-Aminosalicyclic acid is esterified with methanol and HCl followed by acylation of the amine with acetyl chloride/pyridine. The resulting phenol is then O-alkylated with allylbromide under basic conditions in a polar medium to obtain the allylphenyl ether(16). Claisen rearrangement at high temperature results in the methyl 3-allyl-4-acetylaminosalicylates(17). Treatment of the latter with chloromethyl methyl ether in methylene chloride in the presence of potassium t-butoxide gives the O-methoxymethylethers(18). The allyl derivatives(18) are next converted to the aldehydes(19) using sodium periodate and catalytic osmium tetroxide. Treatment of the resulting aldehyde(19) with 2-tetrahydropyranyloxyethyl triphenylphosphonium bromide/-BuLi results in formation of the olefin(20) upon hydrolysis of the methoxymethyl and tetrahydropyranyl ethers. Following catalytic hydrogenation of the double bond, tosylation of the primary alcohol and cyclization with sodium hydride the methyl 6-acetylamino-2,3,4,5-tetrahydro-1-benzoxepin-9-carboxylates result. The latter may be hydrolyzed and deacetylated with aqueous base (such as 10% sodium hydroxide) in polar solvent at raised temperatures to obtain the desired 6-amino-2,3,4,5-tetrahydro-1-benzoxepin-9-carboxylic acid(23). The above sequence of reactions may also be carried out on 4-loweralkylamino salicylic acid to obtain 6-loweralkylamino-2,3,4,5-tetrahydro-1-benzoxepin-9-carboxylic acid.

Treatment of methyl 6-acetylamino-2,3,4,5-tetrahydro-1-benzoxepin-9-carboxylate with N-chlorosuccinimide or N-bromosuccinimide results in halogenation at the 7-position(24). When compound 24 is treated with base as above hydrolysis gives 6-amino-7-halo-2,3,4,5-tetrahydro-1-benzoxepin-9-carboxylic acid(25).

When $R_1$ is methyl and $R_2$ is hydrogen then the above reactions may be followed using 2-tetrahydropyranyloxypropyl triphenylphosphonium bromide in place of 2-tetrahydropyranyloxyethyl triphenylphosphonium bromide in reaction with the 2-methoxymethyloxy-3-carbomethoxy-6-acetylamino phenylacetaldehyde(19). This results in 2-methyl-6-amino-2,3,4,5-tetrahydro-1-benzoxepin-9-carboxylic acid and 2-methyl-6-amino-7-halo-2,3,4,5-tetrahydro-1-benzoxepin-9-carboxylic acid.

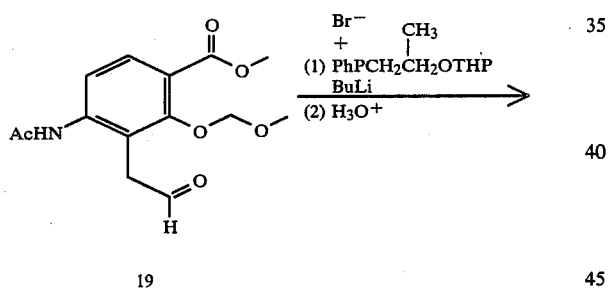

19

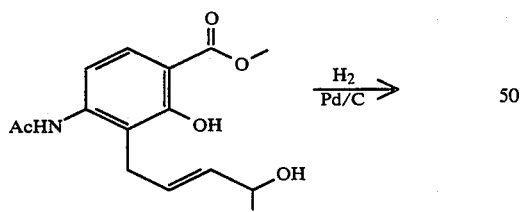

26

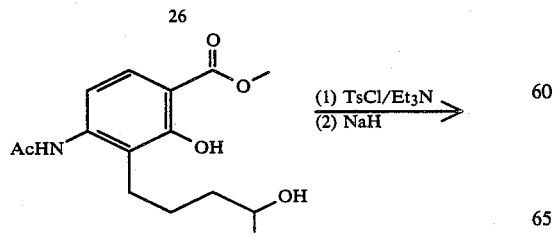

27

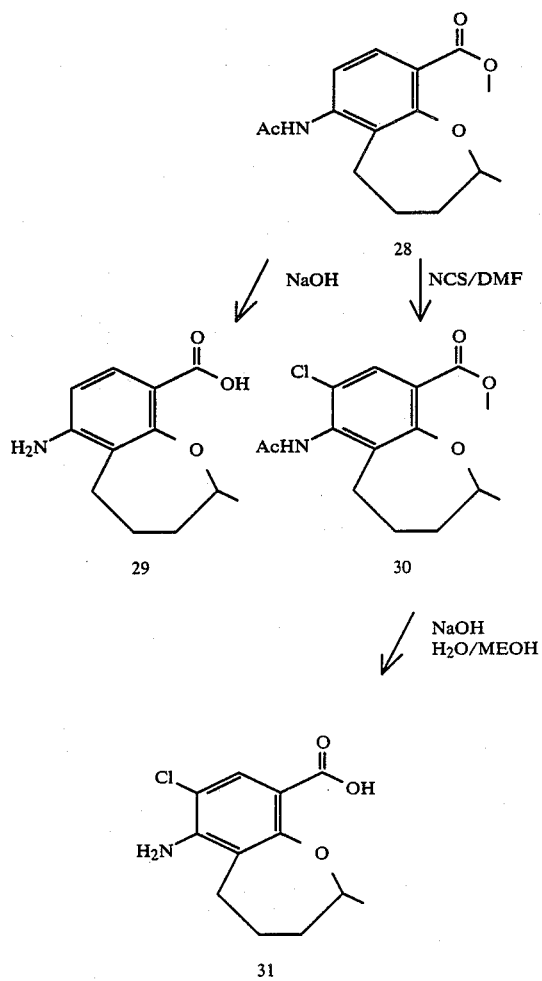

28

29

30

31

Again, it is understood that when it is desired that Y is loweralkylamino, then the above sequence of reactions are carried out with the proper amine.

When $R_1$ and $R_2$ are both substituted such as with methyl groups (35,37), then the Wittig reagent used is

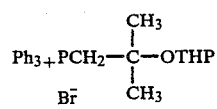

in place of $Ph_3{+}P + CH_2CH_2OTHP$
                               $Br^-$ in the foregoing reaction sequence. Ring closure after reduction is carried out as before with p-tosic acid at raised temperatures.

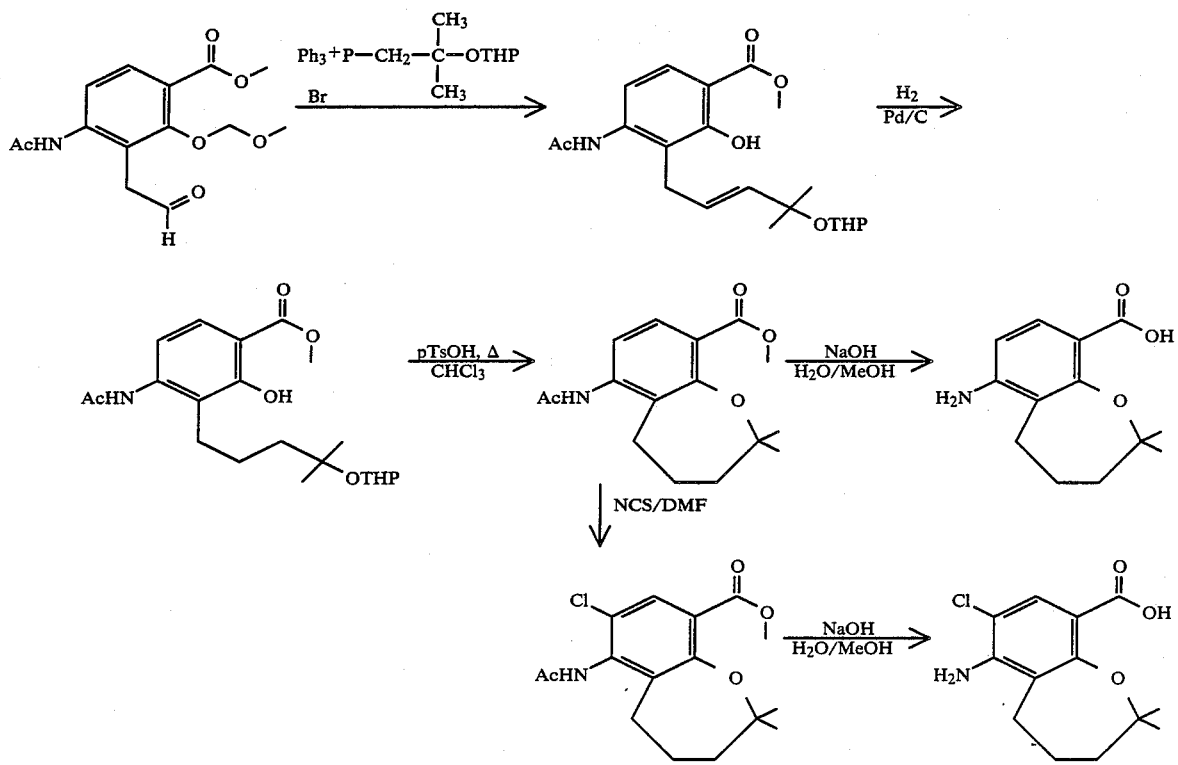

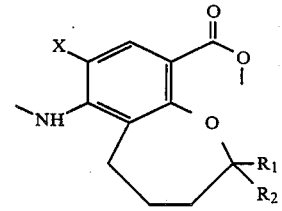

When it is desired that Y is loweralkylamino it is also convenient to deacetylate the 6-acetylamino-9-carbomethoxy compound with sodium methoxide and then react the amine with an alkyliodide to form the alkylamino compound in the usual manner. The ester may then be hydrolyzed with sodium hydroxide as before.

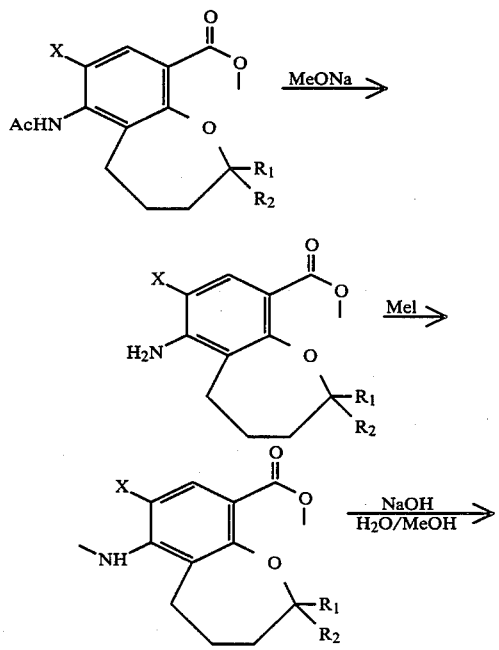

-continued

[structure with X, NH, R1, R2]

The compound of this invention have at least one asymmetric carbon atom and may have two centers when $R_1 \neq R_2$. As a result, the compounds of Formula I may be obtained either as racemic mixtures or as individual enantiomers. When two asymmetric centers are present the product may exist as a mixture of two diastereomers. The product may be synthesized as a mixture of the isomers and then the desired isomer separated by conventional techniques such as chromatography or fractional crystallization from which each diasteromer may be resolved. On the other hand, synthesis may be carried out by known sterospecific processes using the desired form of the intermediate which would result in obtaining the desired specificity.

It is convenient to carry out condensation of the substituted 2,3,4,5-tetrahydro-1-benzoxepin-9-carboxylic acid with 3-amino-1-azabicyclo[2.2.2.]-octane using the sterospecific materials. Thus, the 2-substituted-1-benzoxepin-9-carboxylic acid is resolved prior to condensation with resolved 3-aminoquinuclidine.

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, malic acid, oxalic acid, succinic acid, glycolic acid, lactic acid, salicyclic acid, benzoic acid, nicotinic acid, phthalic acid, stearic acid, oleic acid, abietic acid, etc.

We have found that the compounds of this invention have gastric prokinetic, anti-emetic and lack $D_2$ receptor binding activity and as such possess therapeutic value in the treatment of upper bowel motility and gastroesophageal reflux disorders. Further, the compounds of this invention may be useful in the treatment of disorders related to impaired gastrointestinal motility such as retarded gastric emptying, dyspepsia, flatulence, oesophageal reflux, peptic ulcer and emesis. The compounds of this invention exhibit 5-$HT_3$ antagonism and are considered to be useful in the treatment of psychotic disorders such as schizophrenia and anxiety and in the prophylaxis treatment of migraine and cluster headaches. We have further found that these compounds are selective in that they have little or no dopaminergic antagonist activity.

Various tests in animals can be carried out to show the ability of the compounds of this invention to exhibit pharmacological responses that can be correlated with activity in humans. These tests involve such factors as the effect of the compounds of Formula I on gastric motility, emesis, selective antagonism of 5-$HT_3$ receptors and their $D_2$ dopamine receptor binding properties.

It has been found that the compounds of this invention when tested in the above variety of situations show a marked activity.

One such test is the "Rat Gastric Emptying: Amberlite Bead Method". This test is carried out as follows:

The study is designed to assess the effects of a test agent on gastric emptying of a solid meal in the rat. The procedure is a modification of those used in L. E. Borella and W. Lippmann (1980) *Digestion* 20: 26–49.

PROCEDURE

Amberlite ® beads are placed in a phenol red solution and allowed to soak for several hours. Phenol red serves as an indicator, changing the beads from yellow to purple as their environment becomes more basic. After soaking, the beads are rinsed with 0.1 NaOH to make them purple and then washed with deionized water to wash away the NaOH.

The beads are filtered several times through 1.18 and 1.4 mm sieves to obtain beads with diameters in between these sizes. This is done using large quantities of deionized water. The beads are stored in saline until ready to use.

Male Sprague-Dawley rats are fasted 24 hours prior to the study with water ad libitum. Rats are randomly divided in treatment groups with an N or 6 or 7.

Test agents are prepared in 0.5% methylcellulose and administered to the rats orally in a 10 ml/kg dose volume. Control rats receive 0.5% methylcellulose, 10 ml/kg p.o. One hour after dosing, rats are given 60 Amberlite ® beads intragastrically. The beads are delivered via a 3 inch piece of PE 205 tubing attached to a 16 gauge tubing adapter and syringe. A small piece of PE 50 tubing is placed inside the tubing adapter to prevent the beads from being pulled back into the syringe. The beads are flushed into each rat's stomach with 1 ml saline.

Rats are sacrificed 30 minutes after receiving the beads and their stomachs are removed. The number of beads remaining in each stomach is counted after rinsing the beads with NaOH.

The number of beads remaining in each stomach is subtracted from 60 to obtain the number of beads emptied. The mean number of beads±S.E.M. is determined for each treatment group. The percent change from control is calculated as follows:

$$\frac{\text{Mean Control Group} - \text{Mean Test Agent Group}}{\text{Mean Control Group}} \times 100$$

Statistical significance may be determined using a t-test for independent samples with a probability of 0.05 or less considered to be significant.

In order to demonstrate the ability of the compounds of this invention as anti-emetic agents the following test for "Cisplatin-Induced Emesis in the Ferret" may be used. This test is a modified version of a paper reported by A. P. Florezyk, J. E. Schurig and W. T. Brodner in *Cancer Treatment Reports*: Vol. 66, No. 1. January 1982.

Cisplatin had been shown to cause emesis in the dog and cat. Florczyk, et al. have used the ferret to demonstrate the same effects.

PROCEDURE

Male castrated, Fitch ferrets, weighing between 1.0 and 1.5 kg have an in Indwelling catheter placed in the jagular vein. After a 2–3 day recovery period, the experimental procedure is begun.

30 minutes prior to administration of cisplatin, ferrets are dosed with the compound in 0.9% saline (i.v.) at a dose volume of 2.0 ml/kg.

45 minutes after administration of cisplatin, ferrets are again dosed with the 0.9% saline (i.v.) mixture at a dose volume of 2.0 ml/kg.

Cisplatin is administered (i.v.) 30 minutes after the first dosing with the 0.9% saline. Cisplatin, 10 mg/kg is administered in a dose volume of 2.0 ml/kg.

The time of cisplatin administration is taken as time zero. Ferrets are observed for the duration of the experiment (4 hours). The elapsed time to the first emetic episode is noted and recorded, as are the total number of periods of emesis.

An emetic (vomiting) episode is characterized by agitated behavior, such as pacing around the cage and rapid to and fro movements. Concurrent with this behavior are several retching movements in a row, followed by a single, large, retch which may or may not expulse gastric contents. Immediately following the single large retch, the ferret relaxes. Single coughs or retches are not counted as vomiting episodes.

D-2 Dopamine Receptor Binding Assay

The D-2 dopamine receptor binding assay has been developed with slight modifications using the method of Ian Cresse, Robert Schneider and Solomon H. Snyder, *Europ. J. Pharmacol.* 46: 377–381(1977). Spiroperidol is a butyrophenone neuroleptic whose affinity for dopamine receptors in brain tissue is greater than that of any other known drug. It is a highly specific D-1 dopamine (non-cyclase linked) receptor agent with $K_1$ values of 0.1–0.5 for D-2 inhibition and 300 nM for D-1 inhibition.

Sodium ions are important regulators of dopamine receptors. The affinity of the D-2 receptor is markedly enhanced by the presence of millimolar concentrations of sodium chloride. The Kd in the absence and presence of 120 mM sodium chloride is 1.2 and 0.086 nM respectively. Sodium chloride (120 mM) is included in all assays as a standard condition.

The caudate nucleus (corpus striatum) is used as the receptor source because it contains the highest density of dopamine receptors in the brain and periphery.

PROCEDURE

Male Charles-River rates weighing 250–300 g are decapitated and their brains removed, cooled on ice, and caudate dissected immediately and frozen on dry ice. Tissue can be stored indefinitely at −70° C. For assay caudate is homogenized in 30 ml of tris buffer (pH 7.7 at 25° C.) using the polytron homogenizer. The homogenate is centrifuged at 40,000 g (18,000–19,000 RPM in SS-34 rotor) for 15 minutes. Pellet is resuspended in fresh buffer and centrifuged again. The final pellet is resuspended in 150 volumes of assay buffer.

Specific $^3$H-spiroperidol binding is assayed in a total 2 ml reaction volume consisting of 500 $\mu$l of caudate homogenate, 50 mM tris buffer (pH 7.4 at 35° C.), 5 mM MgSO$_4$, 2 mM EDTA·2NA, 120 mM NaCl, 0.1% ascorbic acid, 0.4 nM $^3$H-spiroperidol and test compound or assay buffer. When catecholamines are included in the assay, 10 $\mu$M pargyline should be included in the reaction mixture to inhibit monoamine oxidase. Samples are incubated at 37° C. for 30 minutes followed by addition of 5 ml ice cold 50 mM TRIS (pH 7.7 at 25° C.) and filtration through GF/B glass fiber filters on a Brandel Receptor Binding Filtration apparatus. Filters are washed twice with an additional 5 ml of tris buffer each. Assay groups are performed in triplicate and 1 $\mu$M d(+) butaclamol is used to determine nonspecific binding. Filters are placed in vials containing 10 ml of Ecoscint phosphor, shaken for 30 minutes and dpm determined by liquid scintillation spectrophotometry using a quench curve. Proteins are determined by the method of Bradford, M. Anal. Biochem 72, 248(1976) using BioRad's coomassie blue G-250 dye reagent. Bovine gamma globulin supplied by BIO-RAD is used as the protein standard.

Bezold-Jarisch Effect in Anaesthetized Rats

Male rats 260–290 g are anaesthetized with urethane 1.25 g/kg$^{-1}$ i.p., and the trachea cannulated. The jugular vein is cannulated for intravenous (i.v.) injection of drugs. Blood pressure is recorded from a cannula in the left carotid artery and connected to a haparin/saline-filled pressure transducer. Continuous heart rate measurements are taken from the blood pressure recordings. The Bezold-Jarisch effect is evoked by rapid, bolus i.v. injections of 5-HT and measurements are made of the fall in heart rate. In each rate, consistent responses are first established with the minimum dose of 5-HT that evokes a clear fall in heart rate. Injections of 5-HT are given every 12 minutes and a dose-response curve for the test compound is established by injecting increasing doses of compound 5 minutes before each injection of 5-HT. The effect of the compound on the 5-HT-evoked brady-cardia is calculated as a percent of the bradycardia evoked by 5-HT before injection of compound.

In separate experiments to measure the duration of 5-HT antagonism caused by the compounds of this invention, a single dose of compound is injected 5 minutes before 5-HT, and the effects of 7 repeated challenges with 5-HT are then monitored. The effects of the compound on the efferent vagal limb of the Bezold-Jarisch reflex are checked by electrically stimulating the peripheral end of a cut vagus nerve. Unipolar electrical stimulation is applied every 5 minutes via a pair of silver electrodes, using 1 ms rectangular pulses in 5 s trains with a maximally-effective voltage (20 V at 10 Hz). Pulse frequency may vary from 5–30 Hz and frequency-response curves are constructed before and 10 minutes after i.v. injection of a single dose of compound.

The results of these above tests indicate that the compounds for this invention exhibit a valuable balance between the peripheral and central action of the nervous system and may be useful in the treatment of disorders related to impaired gastro-intestinal motility such as gastric emptying, dyspepsia, flatulence, esphogal reflux and peptic ulcer and in the treatment of disorders of the central nervous system such as psychosis.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestibel tablets, buccal tablets, troches, capsules, elixirs, suspensions, syrups, wafers, and the like. Such compositions and preprations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelating; excipients such as dicalcium phosphate; a disintegrating agent such as corn starch, patato starch, lginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperiotoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agent delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vaccum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 20 mg or from about 0.01 mg to about 50 mg/kg of body weight per day and higher although it may be administered in several different dosage units from once to several times a day. Higher dosages are required for oral administration.

The compounds of this invention may be prepared by the following representative examples.

EXAMPLE 1

1-Benzoxepin-2-one

To 100 g of m-chloroperbenzoic acid in 1 l of chloroform at 0° C. is added dropwise 100 g of α-tetralone in 250 ml chloroform. After 5 days of stirring at room temperature the reaction mixture is treated carefully with 1 l sat. $NaHCO_3$ and stirred for ½ hour. The organic layer is separated, washed with 500 ml of water and solid $NaHCO_3$ until no evolution of gas. The organic layer is separated washed with sat. $NaHCO_3$ and water and dried ($MgSO_4$). After filtering and concentrating to dryness it is vaccum distilled to obtain low melting material which is used directly in the next step.

EXAMPLE 2

3-(o-Hydroxyphenyl)-1-propanol

To 20 g of lithium aluminum hydride in 200 ml of THF at 0° C. is added dropwise 84 g of 1-benzoxepin-2-one in 200 ml of THF. After addition is complete the reaction mixture is allowed to come to room temperature and stirred 1¼ hours. The reaction mixture is then chilled to 0° C. and 20 ml water, 20 ml 15% of NaOH and 60 ml $H_2O$ are sequentially added. The mixture is then diluted with ethyl acetate, acidified and filtered through celite. The EtOAc layer is separated, dried ($MgSO_4$) and concentrated to obtain 3-(-o-hydroxyphenyl)-1-propanol as a brown oil which is used directly in the next step.

EXAMPLE 3

3-(o-Hydroxyphenyl)-1-tosyloxypropane

To 79.2 g of the diol from Example 2 in 400 ml of methylene chloride is added 100 ml of tiethylamine, followed by 91 g of tosyl chloride in 200 ml methylene chloride. The reaction mixture is stirred at room temperature overnight. The salts are then filtered off and the mixture washed with water, brine and water. The organic layer is dried ($MgSO_4$), filtered and concentrated to obtain 3-(o-hydroxyphenyl)-1-tosyloxypropane as a light brown oil which is used directly in the next step.

EXAMPLE 4

2,3,4,5-Tetrahydro-1-benzoxepin

To a mixture of 18.22 g of sodium hydride (60% dispersed in mineral oil) and 200 ml THF is added dropwise at 0° C. a solution of 146 g of o-tosyloxyphenol in 100 ml of THF. The reaction mixture is allowed to come to room temperature overnight. The reaction mixture is then chilled and 20 ml of $H_2O$ is added slowly. The mixture is then diluted with ethyl acetate and with brine and water. The organic layer is dried ($MgSO_4$), filtered, and concentrated purification by flash column chromatography affords 2,3,4,5-tetrahydro-1-benzoxepin.

EXAMPLE 5

2,3,4,5-tetrahydro-1-benzoxepin-9-carboxylic acid

To 17.6 ml n-butyllithium (2.5 M, 0.044 mol) in 63 ml hexane is added dropwise (0.044 mol) 5.1 g tetramethylethylenediamine (TMEDA) and 5 g (0.034 mol) of 2,3,4,5-tetrahydro-1-benzoxepin. The reaction mixture is stirred overnight. The reaction mixture is then chilled to 0° C. and carbonated with dry ice for an hour. Water (110 ml) is added and the mixture is filtered and the aqueous phase acidified with 4N HCl. The resultant oil is extracted into methylene chloride and dried (MgSO$_4$). After filtering and concentrating in vacuo, 2,3,4,5-tetrahydro-1-benzoxepin-9-carboxylic acid results as a tan solid.

EXAMPLE 6

9-N-(1-Azabicyclo[2.2.2.]octan-3-yl)-carboxamido-2,3,4,5-tetrahydro-1-benzoxepin To an aqueous sodium hydroxide solution of 1.02 g (5.12 mmol) of 3-aminoquinuclidine dihydrochloride and (0.2 g 50% NaOH (0.124 mmol of NaOH solution), is added 6 ml of pyridine and 1.0 g (5.21 mmol) of 2,3,4,5-tetrahydro-1-benzoxepin-9-carboxylic acid. To the resulting mixture is added 1.1 g (5.33 mmol) of N,N'-dicyclohexylcarbodiimide (DCC). This is allowed to stir overnight at room temperature. To this is added an additional 0.2 g of DCC and stirring continued for 2 days. The reaction mixture is filtered, washed with water and the filtrate heated (50° C.) under vaccum to remove the remaining pyridine. Water is added and the reaction mixture again reduced to dryness under vaccum. The residue is treated with dilute NaOH solution to pH≃12. The solution is extracted with methylene chloride. The combined organic layers are then dried (MgSO$_4$) filtered and concentrated to obtain crude 9-N-(1-azabicyclo-[2.2.2.]octan-3-yl)carboxamido-2,3,4,5-tetrahydro-1-benzoxepin which is purified by column chromotagraphy (5:5 methylene chloride/methanol).

Analysis for $C_{18}H_{24}N_2O_2 \cdot \frac{1}{2}H_2O$.
Calculated: C-69.58, H-7.82, N-9.05.
Found: C-70.20, H-7.94, N-8.95.

EXAMPLE 7

7-Chloro-2,3,4,5-tetrahydro-1-benzoxepin-9-carboxylic acid

To a solution of 1.7 g (8.9 mmol) of 2,3,4,5-tetrahydro-1-benzoxepin-9-carboxylic acid in 5 ml of DMF is added 1.41 g (10.6 mmol) of N-chlorosuccinimide (NCS) in one portion at room temperature. The solution is stirred overnight and then diluted with ethyl acetate and washed with water. The organic layer is then dried (MgSO$_4$), filtered and concentrated to obtain 7-chloro-2,3,4,5-tetrahydro-1-benzoxepin-9-carboxylic acid.

EXAMPLE 8

7-Chloro-9-N-(1-azabicyclo[2.2.2.]octan-3-yl)carboxamido-2,3,4,5-tetrahydro-1-benzoxepin To a solution of 100 mg (0.4 mmol) of 7-chloro-2,3,4,5-tetrahydro-1-benzoxepin-9-carboxylic acid in 3 ml chloroform is added 0.073 ml (52 mmol) of triethylamine in one portion at room temperature. The solution is cooled to 0° C. and 0.042 ml (0.44 mmol) of ethylchloroformate is added dropwise. Stirring is continued for 1 hour at 0° C. 3-Aminoquinuclidine dihydrochloride and 796 mg (4 mmol) is dissolved in 3 ml of sat. aq. K$_2$CO$_3$ and the resulting solution cooled to 0° C. The cold aqueous solution is added in one portion to the choloroform solution with vigorous stirring. The reaction mixture is allowed to come to room temperature and stirred overnight. The reaction mixture is diluted with water and extracted with chloroform. The combined organic extracts are dried (MgSO$_4$), filtered and concentrated. Flash chromatography (10% MeOH/CHCl$_3$) removes the impurities to afford 7-chloro-9-N-(1-azabicyclo[2.2.2.]octan-3-yl)carboxamido-2,3,4,5-tetrahydro-1-benzoxepin (M.P. 133°–134.5° C.). carboxamido-2,3,4,5-tetrahydro-1-benzoxepin (M.P. 133°–134.5° C.).

EXAMPLE 9

5-(o-Hydroxyphenyl)-2-methyl-1-pentanol

To a solution of 5 g (31 mmol) of 1-benzoxepin-2-one in 50 ml of ether is added dropwise a solution of 62 mmol (2 eq) of methyl magnesium bromide in ether at 0° C. After addition is completed the reaction mixture is stirred 1 hour at 0° C. and acidified slowly at 0° C. with 1N HCl (20 ml). The reaction mixture is then diluted with water and extracted with ether. The combined organic extracts are dried (MgSO$_4$), filtered and concentrated to obtain 5-(o-hydroxyphenyl)-2-methyl-2-pentanol as a colorless oil which is used directly in the next step.

EXAMPLE 10

2,2-Dimethyl-2,3,4,5-tetrahydro-1-benzoxepin

To a solution of 100 mg (0.52 mmol) 5-(o-hydroxyphenyl)-2-methyl-2-pentanol in 2 ml chloroform is added 25 mg (25 wt %) of p-tosic acid in one portion. The resulting solution is then heated at 80° C. for 2 hours. The reaction mixture is then diluted with methylene chloride and washed with a sat. solution of sodium bicarbonate. The organic layer is dried (MgSO$_4$), filtered and concentrated to obtain 2,2-dimethyl-2,3,4,5-tetrahydro-1-benzoxepin which is used directly in the next step.

EXAMPLE 11

2,2-Dimethyl-2,3,4,5-tetrahydro-1-benzoxepin-9-carboxylic acid

To a solution of 23.18 mmol (1.2 eq) of n-butyl lithium (9.3 ml of 2.5 M solution in hexanes) is added or 3.45 ml (23.18 mmol) of tetramethylethylenediamine dropwise at room temperature. To this resulting solution is added 3.4 g (19.32 mmol) of 2,2-dimethyl-2,3,4,5-tetrahydro-1-benzoxepin. After stirring for 18 hours the reaction mixture is cooled to 0° C., 20 ml hexane added and gaseous CO$_2$ bubbled into the mixture for 1 hour. At this time sufficient water is added to dissolve all the salts. The hexanes are then removed and the aqueous layer washed with hexane. The aqueous layer is acidified to about pH 2 with 3N HCl and extracted with methylene chloride. The combined organic extracts are dried (MgSO$_4$), filtered and concentrated to dryness to obtain 2,2-dimethyl-2,3,4,5-tetrahydro-1-benzoxepin-9-carboxylic acid as a colorless oil.

EXAMPLE 12

2,2-Dimethyl-7-chloro-2,3,4,5-tetrahydro-1-benzoxepin-9-carboxylic acid

To a solution of 3.6 g (16.4 mmol) of 2,2-dimethyl-2,3,4,5-tetrahydro-1-benzoxepin-9-carboxylic acid in 20 ml of DMF is added 2.6 g (19.7 mmol) of N-chlorosuccinimide in one portion at room temperature. The resulting solution is stirred for 3½ days. The reaction mixture is then diluted with ethyl acetate washed with water, and the organic layer is dried (MgSO$_4$), filtered and concentrated to obtain 2,2-dimethyl-7-chloro-2,3,4,5-tetrahydro-1-benzoxepin-9-carboxylic acid.

EXAMPLE 13

2,2-Dimethyl-7-chloro-9-N-(1-azabicyclo[2.2.2.]octan-3-yl)carboxamido-2,3,4,5-tetrahydro-1-benzoxepin To a solution of 250 mg (1 mmol) 2,2-dimethyl-7-chloro-2,3,4,5-tetrahydro-1-benzoxepin-9-carboxylic acid in 3 ml of chloroform is added 0.21 ml (1.5 mmol) of triethylamine in one portion at room temperature. The solution is cooled to 0° C. and ethyl chloroformate is added dropwise. Stirring is continued for 1 hour at 0° C. A cold (ice bath) solution of 3-aminoquinuclidine dihydrochloride and 2 g. (1 mmol) in 3 ml of sat. $K_2CO_3$ is added in one portion and stirring continued at room temperature for 5 hours. The reaction mixture is diluted with water and extracted with chloroform. The combined organic extracts are dried (MgSO$_4$), filtered and concentrated. Flash chromatography (10% MeOH/CHCl$_3$) gives pure 2,2-dimethyl-7-chloro-9-N-(1-azabicyclo[2.2.2.]octan-3-yl)carboxamido-2,3,4,5-tetrahydro-1-benzoxepin which is crystalized from MeOH/ether (M.P. 55°–56° C.).

EXAMPLE 14

When Examples 9, 2, 10 and 11 are followed stepwise but 1 eq of Grignard reagent is used in Example 9 then the product obtained in Example 11 is 2-methyl-2,3,4,5-tetrahydro-1-benzoxepin-9-carboxylic acid.

EXAMPLE 15

Following the chorinating procedures of Example 12 but starting with 2-methyl-2,3,4,5-tetrahydro-1-benzoxepin-9-carboxylic acid in place of 2,2-dimethyl-2,3,4,5-tetrahydro-1-benzoxepin-9-carboxylic acid, the product obtained is 2-methyl-7-chloro-2,3,4,5-tetrahydro-1-benzoxepin-9-carboxylic acid.

EXAMPLE 16

When the procedure of Example 13 is followed but the carboxylic acids prepared by Examples 11, 14 and 15 are used in place of 2,2-dimethyl-7-chloro-2,3,4,5-tetrahydro-1-benzoxepin-9-carboxylic acid then the products prepared are:

2,2-dimethyl-9-N-(1-azabicyclo[2.2.2.]octan-3-yl)-carboxamido-2,3,4,5-tetrahydro-1-benzoxepin 2-methyl-9-N-(1-azabicyclo[2.2.2.]octan-3-yl)-carboxamido-2,3,4,5-tetrahydro-1-benzoxepin and 2,2-methyl-7-chloro-9-N-(1-azabicyclo[2.2.2.]-octan 3-yl)carboxamido-2,3,4,5-tetrahydro-1-benzoxepin

EXAMPLE 17

Methyl 4-aminosalicylate

To a solution of 25 g (118.5 mmol) of 4-aminosalicylic acid sodium salt in 250 ml of methanol is bubbled in anhydrous HCl gas at room temperature. Addition of HCl gas is continued for 30 minutes. Excess methanol is removed in vacuo and the residue taken up in ethyl acetate and washed with saturated aqueous NaHCO$_3$. The organic layer is dried over MgSO$_4$, filtered and concentrated, giving methyl 4-aminosalicylate which is used directly in the next step.

EXAMPLE 18

Methyl 4-acetylaminosalicylate

To a solution of 10 g (59.9 mmol) of methyl 4-aminosalicylate in 100 ml of CH$_2$Cl$_2$ is added 6.8 ml (83.9 mmol) of pyridine in one portion at room temperature. The solution is cooled to 0° C. and 4.7 ml (65.9 mmol) of acetyl chloride is added dropwise. After addition is complete the reaction mixture is let stand 30 minutes at room temperature. The reaction mixture is diluted with water and extracted with CH$_2$Cl$_2$. The combined organic extracts are dried over MgSO$_4$, filtered and concentrated to provide methyl 4-acetylaminosalicylate which is used directly in the next step.

EXAMPLE 19

Methyl 2-allyloxy-4-acetylaminobenzoate

To a solution of 10 g (47.8 mmol) of methyl 4-acetylaminosalicylate in 30 ml of DMF is added 19.8 g (143.4 mmol) of finely ground potassium carbonate in a single portion at room temperature, followed by 8.3 ml (95.6 mmol) of allyl bromide in a similar fashion. The reaction mixture is heated to 60° C. and stirred at that temperature for 4 hours. After cooling to room temperature the reaction mixture is diluted with ethyl acetate and washed with water. The organic layer is dried over MgSO$_4$, filtered and concentrated. Flash chromatography (10% ethyl acetate/hexane) provides methyl 2-allyloxy-4-acetylaminobenzoate which can be used directly in the next step.

EXAMPLE 20

Methyl 3-allyl-4-acetylaminosalicylate

A solution of 5 g (20.1 mmol) of the allyl ether from Example 19 in 20 ml of toluene is heated at 200° C. in a sealed tube for 24 hours. After cooling to room temperature a precipitate begins forming and the reaction mixture is cooled further to 0° C. The precipitate is filtered off and allowed to air dry, giving methyl 3-allyl-4-acetylaminosalicylate which can be used directly in the next step.

EXAMPLE 21

Methyl 2-methoxymethyloxy-3-allyl-4-acetylaminobenzoate

To a solution of 10 g (40.2 mmol) of methyl 3-allyl-4-acetylaminosalicylate in 50 ml of CH$_2$Cl$_2$ is added 7.9 ml (56.3 mmol) of triethylamine in one portion at room temperature, followed by 3.3 ml (44.2 mmol) of chloromethyl methyl ether dropwise at room temperature. Stirring is continued for 24 hours at room temperature. The reaction mixture is diluted with ethyl acetate and washed with water. The organic layer is dried over MgSO$_4$, filtered and concentrated. Flash chromatography (10% EtOAc/hexanes) affords pure methyl 2-methoxymethyloxy-3-allyl-4-acetylaminobenzoate.

EXAMPLE 22

2-Methoxymethyloxy-3-carbomethoxy-6-acetylaminophenylacetaldehyde

A solution of 5 g (17.1 mmol) of methyl 2-methoxymethyloxy-3-allyl-4-acetylaminobenzoate in 20 ml of 1,4-dioxane is heated to 45° C. and 0.86 ml (6.86 mmol) of a 1M solution of osmium tetroxide in t-butanol is added in a single portion. Stirring is continued 15 minutes at 45° C. 7.32 g (34.2 mmol) of sodium periodate is added portionwise and stirring is continued 1 hour. Cyclohexane (1 ml) is added and stirring continued for 1 hour. The reaction mixture is then diluted with $CH_2Cl_2$ and washed with water. The organic layer is dried over $MgSO_4$, filtered and concentrated. Flash chromatography (10% EtOAc/hexanes) affords pure 2-methoxymethyloxy-3-carbomethoxy-6-acetylaminophenylacetaldehyde which is used directly in the next step.

EXAMPLE 23

Methyl 3-(4'-hydroxy-2'-butenyl)-4-acetylaminosalicylate

To a suspension of 9.18 g (20.4 mmol) of 2-tetrahydropyranyloxyethyltriphenylphosphonium bromide in 50 ml of ether is added 7.48 ml (18.7 mmol BuLi) of a 2.5 M solution of butyl lithium in hexanes, dropwise at 0° C. After addition is complete stirring is continued 30 minutes at 0° C. To the solution of the ylide is added a solution of 5 g (17.0 mmol) of the aldehyde from Example 22 in 25 ml of ether dropwise at 0° C. After addition is complete the reaction mixture is allowed to come to room temperature and is stirred 6 hours at room temperature. The reaction mixture is diluted with ether and washed with water. The organic layer is separated and allowed to stand in a refrigerator overnight. The triphenylphospine oxide is filtered off and the ether is removed in vacuo. The residue is dissolved in 25 ml of THF and 25 ml of 6N HCl is added in one portion at room temperature. Stirring is continued for 24 hours at room temperature. THF is removed in vacuo and ethyl acetate is added. The mixture is washed with water, saturated aqueous $NaHCO_3$ and brine. The organic layer is dried over $MgSO_4$, filtered and concentrated. Flash chromatography (20% EtOAc/hexanes) affords methyl 3-(4'-hydroxy-2'-butenyl)-4-acetylaminosalicylate which can be used directly in the next step.

When tetrahydropyranyloxyethyltriphenylphosphonium bromide of Example 23 is replaced with tetrahydropyranyloxypropyltriphenylphosphonium bromide then the product prepared is methyl 3-(4-hydroxy-4'-methyl-2'-butenyl)-4-acetylaminosalicylate.

EXAMPLE 24

Methyl 3-(4'-hydroxybutyl)-4-acetylaminosalicylate

To a solution of 5 g (14.7 mmol) of the olefin from Example 23 in 20 ml of ethyl acetate is added 0.5 g of 10% palladium on carbon in a single portion at room temperature. The reaction mixture is stirred under a positive pressure of hydrogen for 24 hours. The reaction mixture is filtered through celite (washed with ethyl acetate) and concentrated to give methyl 3-(4'-hydroxybutyl)-4-acetylaminosalicylate.

When methyl 3-(4'-hydroxy-2'-butenyl)-4-acetylaminosalicylate in Example 24 is replaced with methyl 3-(4'-hydroxy-4'-methyl-2'-butenyl)-4-acetylaminosalicylate then the product prepared is methyl 3-(4'-hydroxypentyl)-4-acetylaminosalicylate.

EXAMPLE 25

Methyl 3-(4'-Tosyloxybutyl)-4-acetylaminosalicylate

To 1.58 g of methyl 3-(4'-tosyloxybutyl)-4-acetylaminosalicylate in 8 ml of methylene chloride is added 2 ml triethylamine. To this mixture is then added 1.82 g of tosyl chloride in 4 ml methylene chloride and stirred at room temperature overnight. The salts are then filtered off and the mixture washed with water, brine and water and dried ($MgSO_4$). This is then filtered and concentrated to dryness to obtain methyl 3-(4'-tosyloxybutyl)-4-acetylaminosalicylate which is used directly in the next step.

When methyl 3-(4'-hydroxybutyl)-4-acetylaminosalicylate in Example 25 is replaced with methyl 3-(4'-hydroxypentyl)-4-acetylaminosalicylate then the product prepared is methyl 3-(4'-tosyloxypentyl)-4-acetylaminosalicylate.

EXAMPLE 26

Methyl 6-acetylamino-2,3,4,5-tetrahydro-1-benzoxepin-9-carboxylate

To a solution of 5 g (14.6 mmol) of methyl 3-(4'-tosyloxybutyl)-4-acetylaminosalicylate in 50 ml of THF is added 0.64 g (16.1 mmol) of sodium hydride (60% dispersion in mineral oil) portionwise at room temperature. After addition is complete stirring is continued 24 hours at room temperature. Water is added dropwise to decompose excess NaH. The reaction mixture is diluted with ethyl acetate and washed with water. The organic layer is dried over $MgSO_4$, filtered and concentrated. Flash chromatography (5% EtOAc/hexanes) provides methyl 6-acetylamino-2,3,4,5-tetrahydro-1-benzoxepin-9-carboxylate.

When methyl 3-(4'-tosyloxybutyl)-4-acetylaminosalicylate in Example 25 is replaced with 3-(4'-tosyloxypentyl)-4-acetylaminosalicylate then the product prepared is methyl 2-methyl-6-acetylamino-2,3,4,5-tetrahydro-1-benzoxepin-9-carboxylate.

EXAMPLE 27

6-Amino-2,3,4,5-tetrahydro-1-benzoxepin-9-carboxylic acid

To a solution of 5 g (19.0 mmol) of methyl 6-acetylamino-2,3,4,5-tetrahydro-1-benzoxepin-9-carboylate in 10 ml of methanol is added 10 ml of a 10% aqueous solution hydroxide solution in a single portion at room temperature. The reaction mixture is heated to reflux and maintained at that temperature for 2 hours. After cooling, methanol is removed in vacuo and the residue is diluted with water. The pH of the solution is adjusted to 7 with 1N HCl and the solution is extracted with $CH_2Cl_2$. The combined organic extracts are dried over $MgSO_4$, filtered and concentrated. Flash chromatography (30% EtOAc/hexanes) gives 6-amino-2,3,4,5-tetrahydro-1-benzoxepin-9-carboxylic acid.

When methyl 6-acetylamino-2,3,4,5-tetrahydro-1-benzoxepin-9-carboxylate of Example 27 is replaced with methyl 2-methyl-6-acetylamino-2,3,4,5-tetrahydro-1-benzoxepin-9-carboxylate then the product prepared is 2-methyl-6-amino-2,3,4,5-tetrahydro-1-benzoxepin-9-carboxylic acid.

EXAMPLE 28

6-Amino-9-N-(1-azabicyclo[2.2.2.]octan-3-yl)carboxamido-2,3,4,5-tetrahydro-1-benzoxepin To a solution of 1.28 g (6.2 mmol) of 6-amino-2,3,4,5-tetrahydro-1-benzoxepin-9-carboxylic acid in 8 ml of pyridine at 0° C. is added 1.4 g (6.8 mmol) of N,N'-dicyclohexylcarbodiimide in one portion. This is stirred at 0° C. for 1 hour and then 1.23 g (6.2 mmol) 3-aminoquinuclidine dihydrochloride is added in one portion. The mixture is allowed to come to room temperature and stirred overnight. To this is added 8 ml of 1N NaOH and after 30 minutes the reaction mixture is filtered. The filtrate is taken up in methylene chloride, washed with water, dried (MgSO$_4$), filtered and concentrated to dryness to obtain 6-amino-9-N-(1-azabicyclo[2.2.2.]octan-3-yl)-carboxamido-2,3,4,5-tetrahydro-1-benzoxepin.

When 6-amino-2,3,4,5-tetrahydro-1-benzoxepin-9-carboxylic acid of Example 28 is replaced with 2-methyl-6-amino-2,3,4,5-tetrahydro-1-benzoxepin-9-carboxylic acid then the product prepared is 2-methyl-6-amino-9-N-(1-azabicyclo[2.2.2.]octan-3-yl)carboxamido-2,3,4,5-tetrahydro-1-benzoxepin.

EXAMPLE 29

Methyl 6-acetylamino-7-chloro-2,3,4,5-tetrahydro-1-benzoxepin-9-carboxylate

To a solution of 5 g (19.0 mmol) of methyl 6-acetylamino-2,3,4,5-tetrahydro-1-benzoxepin-9-carboxylate from Example 26 in 10 ml DMF is added 3.0 g (22.8 mmol) of N-chlorosuccinimide in a single portion at room temperature. The resulting solution is allowed to stir 24 hours at room temperature. The reaction mixture is diluted with ethyl acetate and washed with water. The organic layer is dried over MgSO$_4$, filtered, concentrated and subjected to flash chromatography (20% EtOAc/hexanes) to yield methyl 6-acetylamino-7-chloro-2,3,4,5-tetrahydro-1-benzoxepin-9-carboxylate. This is used in the next step.

When methyl 6-acetylamino-2,3,4,5-tetrahydro-1-benzoxepin-9-carboxylate of Example 29 is replaced with methyl 2-methyl-6-acetylamino-2,3,4,5-tetrahydro-1-benzoxepin-9-carboxylate then the product prepared is methyl 2-methyl-6-acetylamino-7-chloro-2,3,4,5-tetrahydro-1-benzoxepin-9-carboxylate.

EXAMPLE 30

6-Amino-7-chloro-2,3,4,5-tetrahydro-1-benzoxepin-9-carboxylic acid

To a solution of 5 g (16.8 mmol) of methyl 6-acetylamino-7-chloro-2,3,4,5-tetrahydro-1-benzoxepin-9-carboxylate in 10 ml of methanol is added 10 ml of a 10% aqueous sodium hydroxide solution in a single portion at room temperature. The solution is heated to reflux and maintained for 2 hours. After cooling, methanol is removed in vacuo and the residue is diluted with water. The pH of this solution is adjusted to 7 with 1N HCl. The neutral solution is extracted with CH$_2$Cl$_2$ and the combined organic extracts are dried over MgSO$_4$, filtered and concentrated. Flash chromatography (30% EtOAc/hexanes) provides 6-amino-7-chloro-2,3,4,5-tetrahydro-1-benzoxepin-9-carboxylic acid.

When methyl 6-acetylamino-7-chloro-2,3,4,5-tetrahydro-1-benzoxepin-9-carboxylate of Example 30 is replaced by methyl 2-methyl-6-acetylamino-7-chloro-2,3,4,5-tetrahydro-1-benzoxepin-9-caroxylate then the compound prepared is 2-methyl-6-amino-7-chloro-2,3,4,5-tetrahydro-1-benzoxepin-9-carboxylic acid.

EXAMPLE 31

6-Amino-7-chloro-9-N-(1-azabicyclo[2.2.2.]octan-3-yl)carboxamido-2,3,4,5-tetrahydro-1-benzoxepin To a solution of 900 mg (3.72 mmol) of 6-amino-7-chloro-2,3,4,5-tetrahydro-1-benzoxepin-9-carboxylic acid in 4.8 ml of pyridine at 0° C. is added 900 mg (4.09 mmol) of N,N'-dicyclohexylcarbodiimide in one portion. This is stirred at 0° C. for 1 hour and then 740 mg (3.72 mmol) of 3-aminoquinuclidine dihydrochloride is added in one portion. The mixture is allowed to come to room temperature and stirred overnight. To this is added 4.8 ml of 1N NaOH and after 30 minutes the reaction mixture is filtered. The filtrate is taken up in methylene chloride, washed with water, dried (MgSO$_4$), filtered and concentrated to dryness to obtain 6-amino-7-chloro-9-N-(1-azabicyclo[2.2.2.]octan-3-yl)carboxamido-2,3,4,5-tetrahydro-1-benzoxepin.

When 6-amino-7-chloro-2,3,4,5-tetrahydro-1-benzoxepin-9-carboxylic acid of Example 31 is replaced with 2-methyl-6-amino-7-chloro-2,3,4,5-tetrahydro-1-benzoxepin-9-carboxylic acid then the product prepared is 2-methyl-6-amino-7-chloro-9-N-(1-azabicyclo[2.2.2.]octan-3-yl)carboxamido-2,3,4,5-tetrahydro-1-benzoxepin.

EXAMPLE 32

When 2-tetrahydropyranylpropyltriphenylphosphonium bromide is used in place of 2-tetrahydropyranylethyltriphenylphosphonium bromide in Example 23 and when the succeeding examples 24, 25 and 26 are followed, the product obtained is 2-methyl-6-amino-2,3,4,5-tetrahydro-1-benzoxepin-9-carboxylic acid.

EXAMPLE 33

When methyl 2-methyl-6-acetylamino-2,3,4,5-tetrahydro-1-benzoxepin-9-carboxylate prepared by Example 32 is used in Example 29 in place of methyl 6-acetylamino-2,3,4,5-tetrahydro-1-benzoxepin-9-carboxylate, then the product prepared is methyl 2-methyl-6-acetylamino-7-chloro-2,3,4,5-tetrahydro-1-benzoxepin-9-carboxylate.

EXAMPLE 34

When methyl 2-methyl-6-acetylamino-7-chloro-2,3,4,5-tetrahydro-1-benzoxepin-9-carboxylate is used in place of methyl 6-acetylamino-7-chloro-2,3,4,5-tetrahydro-1-benzoxepin-9-carboxylate in Example 30, then the product prepared is 2-methyl-6-amino-7-chloro-2,3,4,5-tetrahydro-1-benzoxepin-9-carboxylic acid.

EXAMPLE 35

When 2-methyl-6-amino-7-chloro-2,3,4,5-tetrahydro-1-benzoxepin-9-carboxylic acid is used in Example 31 in place of 6-amino-7-chloro-2,3,4,5-tetrahydro-1-benzoxepin-9-carboxylic acid, then the product prepared is 2-methyl-6-amino-7-chloro-9-N-(1-azabicyclo[2.2.2.]octan-3-yl)carboxamido-2,3,4,5-tetrahydro-1-benzoxepin.

EXAMPLE 36

Methyl 3-(2'-methyl-2'-hydroxypentyl)-4-acetylaminosalicylate

To a suspension of 20.4 mmol of

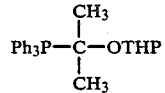

in 50 ml of ether is added 16 ml (20 mmol BuLi) of a 2.5 M solution of butyl lithium in hexanes, dropwise at 0° C. After addition is complete stirring is continued 30 minutes at 0° C. To the solution of the ylide is added a solution of 5 g (17.0 mmol) of the aldehyde from Example 22 in 25 ml of ether dropwise at 0° C. After addition is complete the reaction mixture is allowed to come to room temperature and is stirred 6 hours at room temperature. The reaction mixture is diluted with ether and washed with water. The organic layer is separated and allowed to stand in a refrigerator overnight. The triphenylphospine oxide is filtered off and the ether is removed in vacuo. The residue is dissolved in 25 ml of THF and 25 ml of 6N HCl is added in one portion at room temperature. Stirring is continued for 24 hours at room temperature. THF is removed in vacuo and ethyl acetate is added. The mixture is washed with water, saturated aqueous NaHCO$_3$ and brine. The organic layer is dried over MgSO$_4$, filtered and concentrated. Flash chromatography (20% EtOAc/hexanes) affords methyl 3-(2'-methyl-2'-hydroxypentyl)-4-acetylaminosalicylate.

EXAMPLE 37

Methyl 3-(2'-methyl-2'-tosyloxypentyl)-4-acetylaminosalicylate

To 4 g of the diol from Example 36 in 20 ml of methylene chloride is added 5 ml of triethylamine and 4.55 g of tosyl chloride in 10 ml of methylene chloride. This is stirred at room temperature overnight, filtered, washed with water and dried (MgSO$_4$). This is then filtered and evaporated to dryness to obtain methyl 3-(2'-methyl-2'-tosyloxypentyl)-4-acetylaminosalicylate.

EXAMPLE 38

Methyl 2,2-dimethyl-6-acetylamino-2,3,4,5-tetrahydro-1-benzoxepin-9-carboxylate

To a mixture of 2.2 g sodium hydride (60%) and 20 ml THF is added dropwise at 0° C. a solution of 15 g of methyl 3-(2'-methyl-2'-tosyloxypentyl)-4-acetylaminosalicylate in 10 ml THF. This is allowed to come to room temperature over several hours, then chilled and 2 ml H$_2$O added slowly. This is then diluted with ethyl acetate, the salts filtered off, washed with water and brine, dried and concentrated to dryness to obtain methyl 2,2-dimethyl-6-acetylamino-2,3,4,5-tetrahydro-1-benzoxepin-9-carboxylate which is used directly in the next step.

EXAMPLE 39

2,2-Dimethyl-6-amino-2,3,4,5-tetrahydro-1-benzoxepin-9-carboxylic acid

To a solution of 5.5 g (19.0 mmol) of methyl 2,2-dimethyl-6-acetylamino-2,3,4,5-tetrahydro-1-benzoxepin-9-carboxylate in 10 ml of methanol is added 10 ml of a 10% aqueous sodium hydroxide solution in a single portion at room temperature. The reaction mixture is heated to reflux and maintained at that temperature for 2 hours. After cooling, methanol is removed in vacuo and the residue is diluted with water. The pH of the solution is adjusted to 7 with 1N HCl and the solution is extracted with CH$_2$Cl$_2$. The combined organic extracts are dried over MgSO$_4$, filtered and concentrated. Flash chromatography (30% EtOAc/hexanes) gives 2,2-dimethyl-6-amino-2,3,4,5-tetrahydro-1-benzoxepin-9-carboxylic acid.

EXAMPLE 40

2,2-Dimethyl-6-amino-9-N-(1-azabicyclo[2.2.2.]octan-3-yl)carboxamido-2,3,4,5-tetrahydro-1-benzoxepin To a solution of 1.45 g (6.2 mmol) of 2,2-dimethyl-6-amino-2,3,4,5-tetrahydro-1-benzoxepin-9-carboxylic acid in 8 ml of pyridine at 0° C. is added 1.4 g (6.8 mmol) of N,N'-dicyclohexylcarbodiimide in one portion. This is stirred at 0° C. for 1 hour and then 1.23 g (6.2 mmol) 3-aminoquinuclidine dihydrochloride is added in one portion. The mixture is allowed to come to room temperature and stirred overnight. To this is added 8 ml of 1N NaOH and after 30 minutes the reaction mixture is filtered. The filtrate is taken up in methylene chloride, washed with water, dried (MgSO$_4$), filtered and concentrated to dryness to obtain 2,2-dimethyl-6-amino-9-N-(1-azabicyclo[2.2.2.]octan-3-yl)carboxamido-2,3,4,5-tetrahydro-1-benzoxepin.

EXAMPLE 41

Methyl 2,2-dimethyl-6-acetylamino-7-chloro-2,3,4,5-tetrahydro-1-benzoxepin-9-carboxylate To a solution of 5.5 g (19.0 mmol) of methyl 2,2-dimethyl-6-acetylamino-2,3,4,5-tetrahydro-1-benzoxepin-9-carboxylate from Example 37 in 10 ml DMF is added 3.0 g (22.8 mmol) of N-chlorosuccinimide in a single portion at room temperature. The resulting solution is allowed to stir 24 hours at room temperature. The reaction mixture is diluted with ethyl acetate and washed with water. The organic layer is dried over MgSO$_4$, filtered, concentrated and subjected to flash chromatography (20% EtOAc/hexanes) to yield methyl 2,2-dimethyl-6-acetylamino-7-chloro-2,3,4,5-tetrahydro-1-benzoxepin-9-carboxylate. This is used directly in the next step.

EXAMPLE 42

2,2-Dimethyl-6-amino-7-chloro-2,3,4,5-tetrahydro-1-benzoxepin-9-carboxylic acid

To a solution of 5.46 g (16.8 mmol) of methyl 2,2-dimethyl-6-acetylamino-7-chloro-2,3,4,5-tetrahydro-1-benzoxepin-9-carboxylate in 10 ml of methanol is added 10 ml of a 10% aqueous sodium hydroxide solution in a single portion at room temperature. The solution is heated to reflux and refluxing maintained for 2 hours. After cooling, methanol is removed in vacuo and the residue is diluted with water. The pH of this solution is adjusted to 7 with 1N HCl. The neutral solution is extracted with CH$_2$Cl$_2$ and the combined organic extracts are dried over MgSO$_4$, filtered and concentrated. Flash chromatography (30% EtOAc/hexanes) provides 2,2-dimethyl-6-amino-7-chloro-2,3,4,5-tetrahydro-1-benzoxepin-9-carboxylic acid.

EXAMPLE 43

2,2-Dimethyl-6-amino-7-chloro-9-N-(1-azabicyclo[2.2.2.]octan-3-yl)carboxamido-2,3,4,5-tetrahydro-1-benzoxepin To a solution of 1 g (3.72 mmol) of 2,2-dimethyl-6-amino-7-chloro-2,3,4,5-tetrahydro-1-benzoxepin-9-carboxylic acid in 4.8 ml of pyridine at 0° C. is added 900 mg (4.09 mmol) of N,N'-dicyclohexylcarbodiimide in one portion. This is stirred at 0° C. for 1 hour and then 740 mg (3.72 mmol) of 3-aminoquinuclidine dihydrochloride is added in one portion. The mixture is allowed to come to room temperature and stirred overnight. To this is added 4.8 ml of 1N NaOH and after 30 minutes the reaction mixture is filtered. The filtrate is taken up in methylene chloride, washed with water, dried (MgSO$_4$), filtered and concentrated to dryness to obtain 2,2-dimethyl-6-amino-7-chloro-9-N-(1-azabicyclo-[2.2.2.]-octan-3-yl)-carboxamido-2,3,4,5-tetrahydro-1-benzoxepin.

EXAMPLE 44

When N-chlorosuccinimide of Examples 7, 12 15, 29 and 41 is replaced by N-bromosuccinimide then the corresponding bromo compounds are obtained.

EXAMPLE 45

When methyl 4-aminosalicylate of Example 17 is replaced with methyl 4-methylaminosalicylate then the corresponding methylamino product is obtained in Examples 17 through 44.

We claim:

1. A compound of the formula:

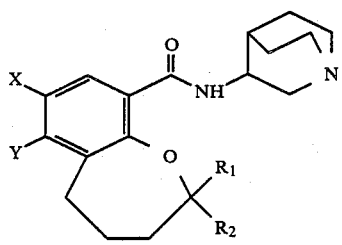

where:
X is hydrogen or halo;
Y is hydrogen, amino or loweralkylamino;
$R_1$ and $R_2$ are independently hydrogen or loweralkyl;
or a pharmaceutically acceptable thereof.

2. A compound according to claim 1 where X is halo and Y, $R_1$ and $R_2$ are hydrogen.

3. A compound according to claim 1 where Y is amino or loweralkylamino and X, $R_1$ and $R_2$ are hydrogen.

4. A compound according to claim 1 where X is halo, Y is amino or loweralkylamino and $R_1$ and $R_2$ are hydrogen.

5. A compound according to claim 2 where X is chloro thus forming 7-chloro-9-N-(1-azabicyclo[2.2.2.]octan-3-yl)-carboxamido-2,3,4,5-tetrahydro-1-benzoxepin.

6. A compound according to claim 2 where X is bromo thus forming 7-bromo-9-N-(1-azabicyclo[2.2.2.]octan-3-yl)-carboxamido-2,3,4,5-tetrahydro-1-benzoxepin.

7. A compound according to claim 3 where Y is amino thus forming 6-amino-9-N-(1-azabicyclo[2.2.2.]octan-3-yl)-carboxamido-2,3,4,5-tetrahydro-1-benzoxepin.

8. A compound according to claim 3 where Y is methylamino thus forming 6-methylamino-9-N-(1-azabicyclo[2.2.2.]octan-3-yl)carboxamido-2,3,4,5-tetrahydro-1-benzoxepin.

9. A compound according to claim 4 where X is chloro and Y is amino thus forming 6-amino-7-chloro-9-N-(1-azabicyclo[2.2.2.]octan-3-yl)carboxamido-2,3,4,5-tetrahydro-1-benzoxepin.

10. A compound according to claim 4 where X is bromo and Y is amino thus forming 6-amino-7-bromo-9-N-(1-azabicyclo[2.2.2.]octan-3-yl)carboxamido-2,3,4,5-tetrahydro-1-benzoxepin.

11. A compound according to claim 1 where X is hydrogen, Y is hydrogen and $R_1$ and $R_2$ are methyl thus forming 2,2-dimethyl-9-N-(1-azabicyclo[2.2.2.]octan-3-yl)carboxamido-2,3,4,5-tetrahydro-1-benzoxepin.

12. A compound according to claim 1 where X is chloro, Y is hydrogen and $R_1$ and $R_2$ are methyl thus forming 2,2-dimethyl-7-chloro-9-N-(1-azabicyclo-[2.2.2.]octan-3-yl)carboxamido-2,3,4,5-tetrahydro-1-benzoxepin.

13. A method for the treatment of gastric prokinetic disorders in humans and mammals comprising administering thereto an effective amount of a compound of the formula according to claim 1.

14. A method for the treatment of emesis in humans and mammals comprising administering thereto an effective amount of a compound of the formula according to claim 1.

* * * * *